US008124033B2

(12) United States Patent
Neuzil et al.

(10) Patent No.: US 8,124,033 B2
(45) Date of Patent: Feb. 28, 2012

(54) APPARATUS FOR REGULATING THE TEMPERATURE OF A BIOLOGICAL AND/OR CHEMICAL SAMPLE AND METHOD OF USING THE SAME

(75) Inventors: Pavel Neuzil, Singapore (SG); Tseng-Ming Hsieh, Singapore (SG); Juergen Pipper, Singapore (SG)

(73) Assignee: Agency, Science, Technology and Research, Singapore (SG)

( * ) Notice: Subject to any disclaimer, the term of this patent is extended or adjusted under 35 U.S.C. 154(b) by 1040 days.

(21) Appl. No.: 11/356,511

(22) Filed: Feb. 17, 2006

(65) Prior Publication Data
US 2007/0196237 A1    Aug. 23, 2007

(51) Int. Cl.
*B01L 9/00*    (2006.01)
(52) U.S. Cl. ........ 422/561; 422/560; 422/563; 422/566; 436/157
(58) Field of Classification Search ............ 422/99, 422/102, 104, 560, 561, 563, 547, 551, 552, 422/553; 435/303.1, 305.1; 436/155, 157
See application file for complete search history.

(56) References Cited

U.S. PATENT DOCUMENTS

| | | | |
|---|---|---|---|
| 5,498,312 A | | 3/1996 | Laermer et al. |
| 5,601,141 A | * | 2/1997 | Gordon et al. .............. 165/263 |
| 6,146,882 A | * | 11/2000 | Uematsu et al. ........... 435/303.1 |
| 6,392,206 B1 | * | 5/2002 | Von Arx et al. ............ 219/468.1 |
| 6,509,186 B1 | | 1/2003 | Zou et al. |
| 6,692,700 B2 | * | 2/2004 | Handique .................... 422/102 |
| 7,049,558 B2 | * | 5/2006 | Baer et al. ..................... 219/548 |
| 7,189,367 B2 | * | 3/2007 | Yamamoto et al. .......... 422/100 |
| 7,682,571 B2 | * | 3/2010 | Kim et al. .................... 422/102 |
| 2005/0006372 A1 | | 1/2005 | Murakami et al. ........... 219/385 |
| 2005/0022261 A1 | | 1/2005 | Fincher et al. ............... 800/278 |
| 2005/0028587 A1 | | 2/2005 | Baer et al. ................. 73/204.26 |
| 2005/0247701 A1 | | 11/2005 | Deka et al. .................... 219/548 |

FOREIGN PATENT DOCUMENTS
WO    WO 2005/105292    11/2005

OTHER PUBLICATIONS

Cady et al., "Real-time PCR detection of *Listeria monocytogenes* using an integrated microfluidics platform", *Sensors and Actuators B* 107(2005) 332-341.

(Continued)

*Primary Examiner* — Jill Warden
*Assistant Examiner* — Dwayne K Handy
(74) *Attorney, Agent, or Firm* — Stout, Uxa, Buyan & Mullins; Carlos A. Fisher

(57) ABSTRACT

The invention provides an apparatus for regulating the temperature of a chemical and/or biological sample and a method of using the same. The apparatus includes at least one temperature control module. The temperature control module includes a heater, a conductor of caloric, and a temperature sensor. The heater of the temperature control module is adapted to thermally communicate with a removable substrate, on which said chemical and/or biological sample is placed, via the conductor of caloric. The temperature sensor of the temperature control module is adapted to detect and control the temperature of the substrate via the conductor of caloric. The apparatus is designed such that the substrate is situated above said temperature control module to entirely cover said temperature control module.

18 Claims, 8 Drawing Sheets

OTHER PUBLICATIONS

Dasgupta et al., "Light emitting diode-based detectors Absorbance, fluorescence and spectroelectrochemical measurements in a planar flow-through cell", *Analytica Chemica Acta* 500 (2003) 337-364.

Fixman et al., "Theory of DNA Melting Curves", *Biopolymers*, vol. 16, (1977) 2693-2704.

Guttenberg et al., "Planar chip device for PCR and hybridization with surface acoustic wave pump", *Lab Chip*, vol. 5 (2005), 308-317.

Kim et al., 2003 ECI Conference on Heat Exchanger Fouling and Cleaning: Fundamentals and Applications (2003) vol. RP1, 107-114.

Lyon et al., "Quantification of HER2/neu Gene Amplification by Competitive PCR Using Fluorescent Melting Curve Analysis", *Clinical Chemistry*, (2001) vol. 47:5, 844-851.

Matsuda et al., "Phosphorylcholine-endcapped oligomer and block co-oligomer and surface biological reactivity", *Biomaterials* (2003) vol. 24, 4517-4527.

Neuzil et al., "Evaluation of thermal parameters of bolometer devices", *Applied Physics Letters*, (2002) vol. 80, No. 10, 1838-1840.

Rutledge, R.G., "Sigmoidal curve-fitting redefines quantitative real-time PCR with the prospective of developing automated high-throughput applications", *Nucleic Acids Research*, (2004) vol. 32, No. 22, e178, eight pages.

Wilkening et al., "Quantitative Real-Time Polymerase Chain Reaction: Methodical Analysis and Mathematical Model", *Journal of Biomolecular Techniques* (2004) vol. 15, Issue 2, 107-111.

\* cited by examiner

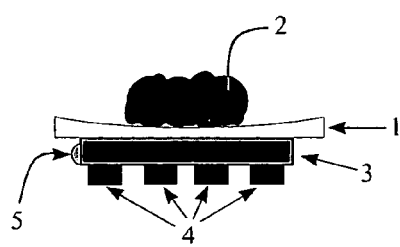
Fig. 3A
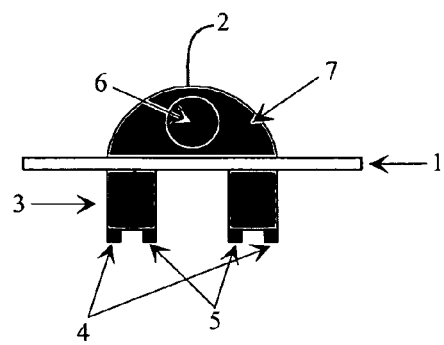
Fig. 3B
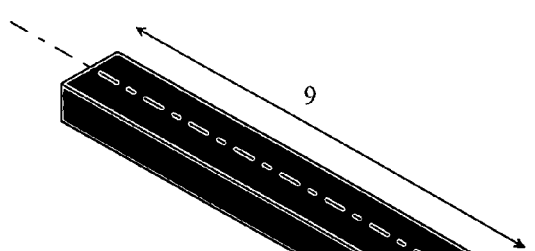
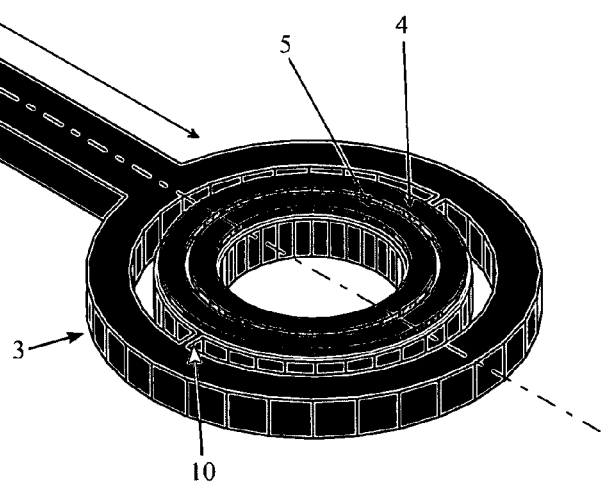
Fig. 4
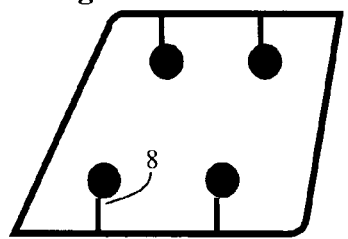
Fig. 5A
Fig. 5B
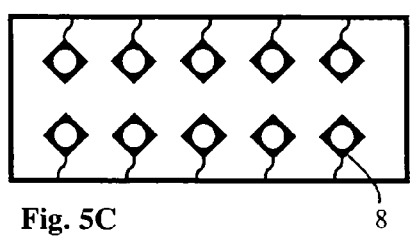
Fig. 5C
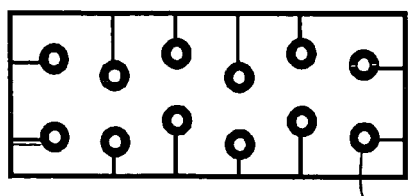
Fig. 5D

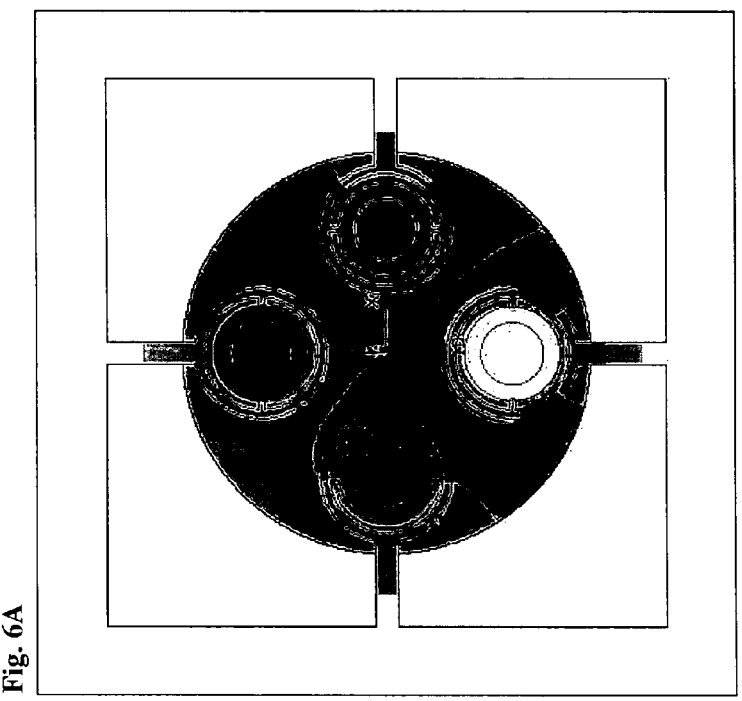
Fig. 6A
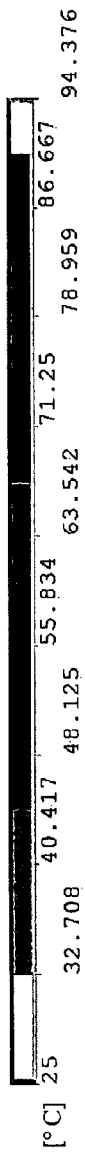
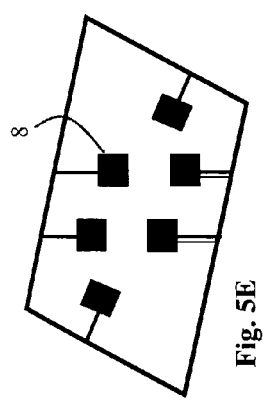
Fig. 5E
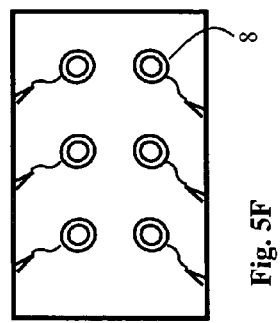
Fig. 5F

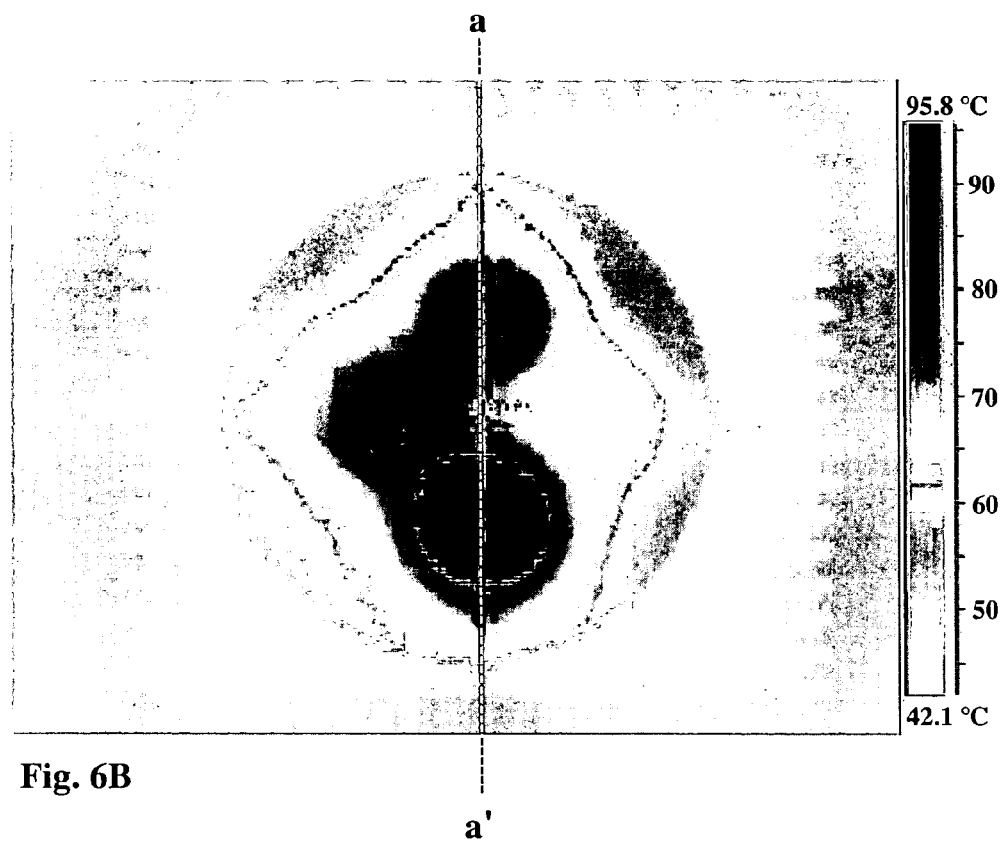
Fig. 6B
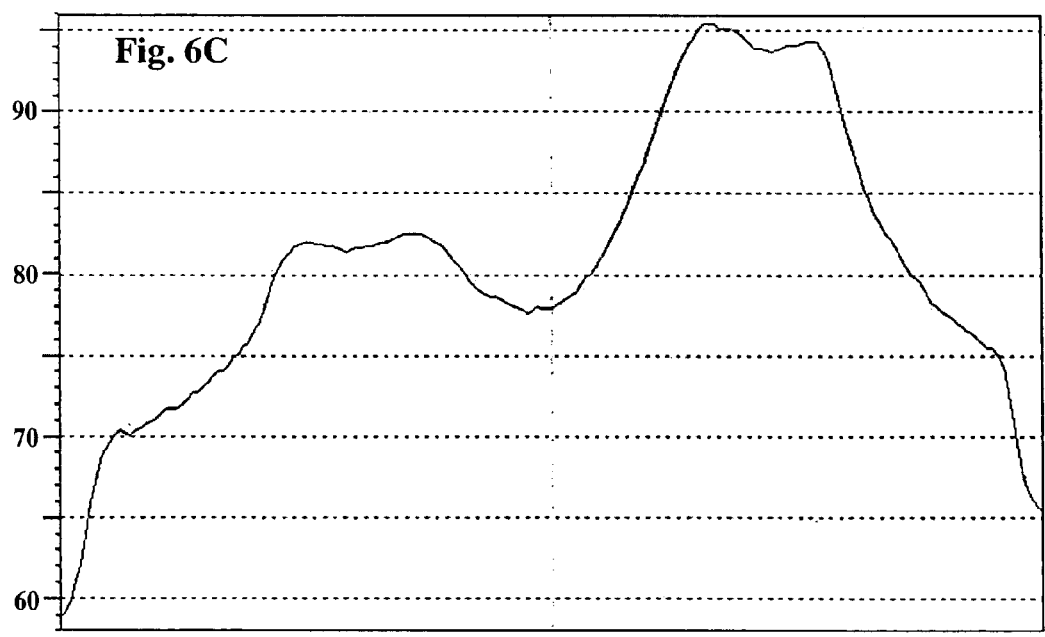

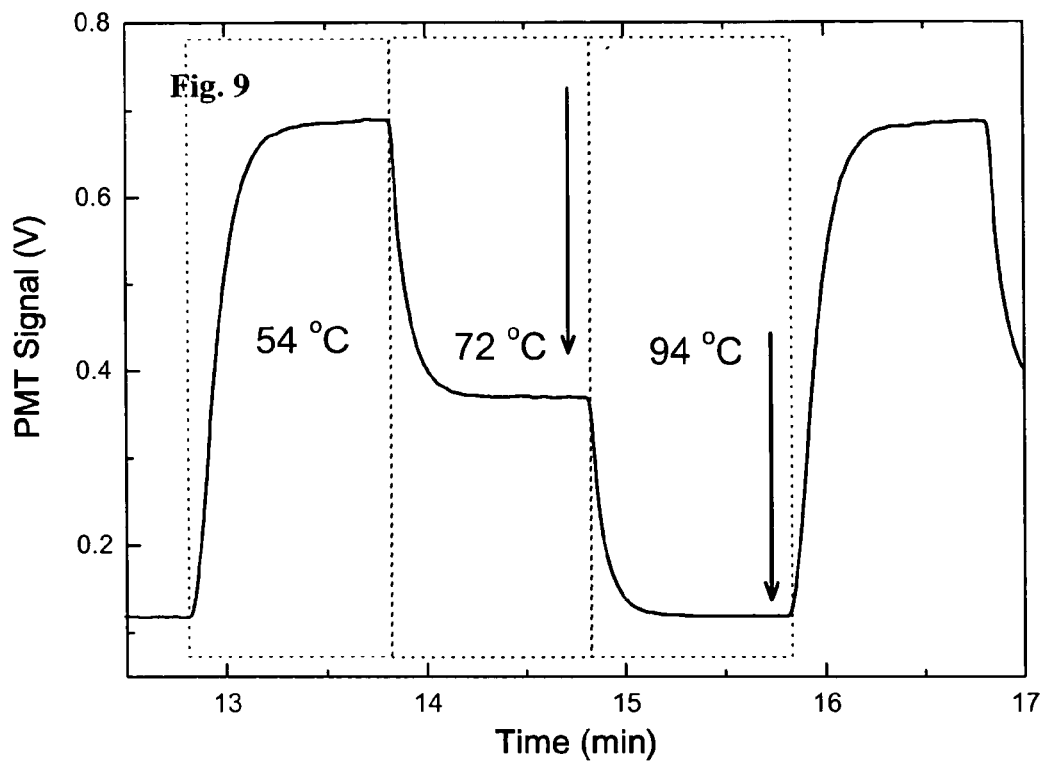
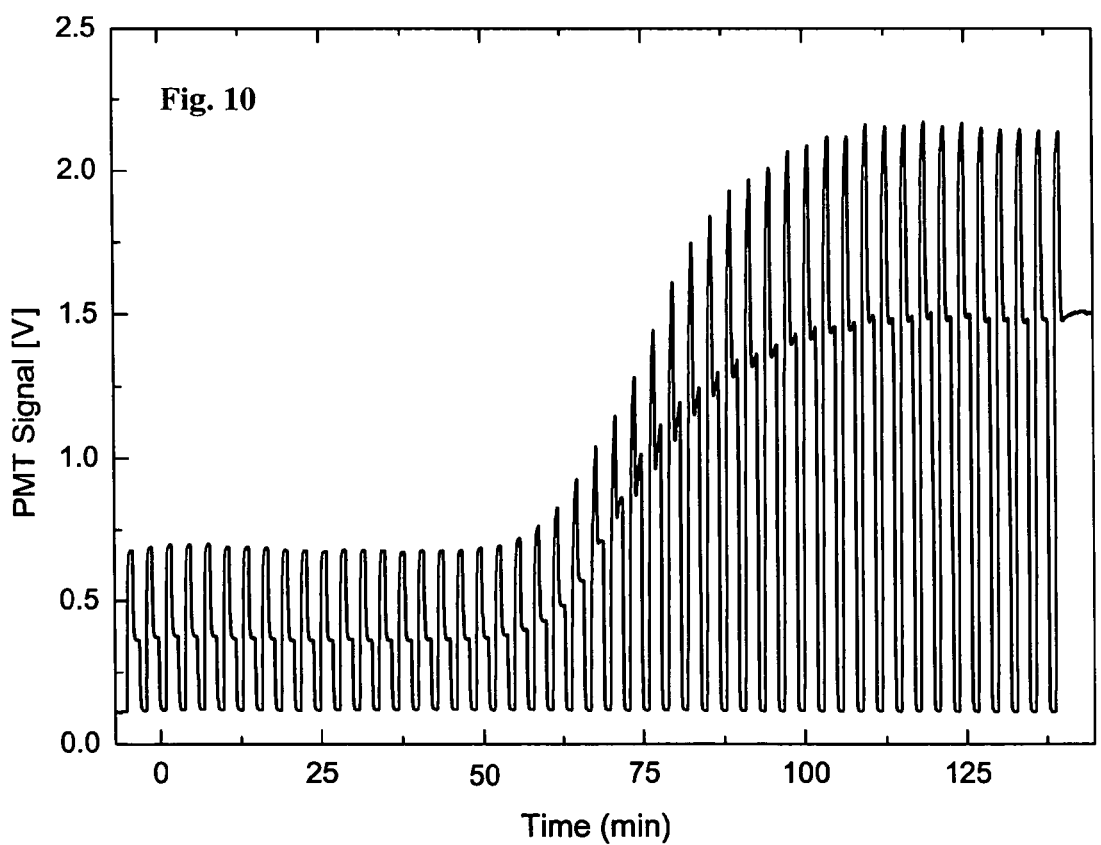

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_binding
<222> LOCATION: (1)..(23)

<400> SEQUENCE: 1
ctcatttcct ggtatgacaa cga                                           23

<210> SEQ ID NO 2
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_binding
<222> LOCATION: (1)..(23)

<400> SEQUENCE: 2
gtctacatgg caactgtgag gag                                           23
```

APPARATUS FOR REGULATING THE TEMPERATURE OF A BIOLOGICAL AND/OR CHEMICAL SAMPLE AND METHOD OF USING THE SAME

FIELD OF THE INVENTION

The present invention relates to an apparatus for regulating the temperature of a biological and/or chemical sample, particularly a sample in a liquid droplet.

BACKGROUND OF THE INVENTION

Numerous diagnostic, analytical and preparative procedures include steps in which temperature changes are effected. To achieve reproducible and accurate results it is required to maintain control of the temperature of a reaction mixture, such as a sample, and to maintain temperature uniformity within the respective reaction mixture. Further, many diagnostic, analytical and preparative procedures rely on enzymes, which show an optimal performance at a defined temperature. To obtain exact temperature control it is generally required to provide a close contact between the reaction mixture and the heating or cooling element. At the same time cross-contaminations of different reaction mixtures, e.g. samples, need to be avoided.

An example of a process in which controlled heating and maintenance of temperature uniformity are particularly important is in vitro nucleic acid amplification by means of the polymerase chain reaction (PCR). Typically the PCR process is a thermal cycling process, wherein the basic cycle can be divided into three steps: (a) separation of the DNA double-strand at about 90° C. to about 94° C. (b) cooling down to about 50° C.-70° C. to renaturate the specific primers to the single stranded DNA (annealing), and (c) increasing the temperature to about 70° C.-80° C. for extension of the primers with thermostable DNA polymerase (elongation).

Temperature control during a PCR reaction is typically performed by a feedback loop system, while temperature uniformity is achieved by highly thermally conductive but bulky materials such as copper. In addition to temperature control and maintenance of temperature uniformity within the sample, it is also important to provide a sample heating (cooling) rate of at least 5 K/s (−5 K/s). A high heating rate is accomplished by the implementation of a Proportional Integrated Derivative (PID) control system limited by maximum dissipated power and heat capacitance. A high cooling rate is rather difficult to achieve and bulky systems require force cooling by either a Thermoelectric Element (TEC, often called Peltier element) or by other means, such as water. Such devices are complicated and power hungry.

As the systems are bulky, their thermal time constants are in minutes rather than seconds. That results in long transition times and unwanted by-products of the PCR reaction. The high power consumption furthermore eliminates the possibility of making a battery-operated and portable PCR system. In addition, the reaction tubes are large and the required amount of PCR cocktail renders the entire process cost-intensive. Furthermore, the detection of PCR product has to be done off-line, i.e. by employing another device, resulting in additional costs.

While the systems currently used to carry out PCR reactions allow for running multiple samples at the same time, they do not allow for individual temperature control of different samples. Where it is desired to expose samples to varying temperature cycle conditions, several systems therefore have to be employed in parallel. It is therefore desirable to provide an apparatus that is able to simultaneously handle samples individually during PCR.

Miniaturization of devices in the chemical, pharmaceutical and biotechnological field has lead to the development of microfluidic devices and microarrays. Accordingly, micro PCR methods (µPCR) are being developed, which are expected to become a central part of a Lab-on-a-Chip or micro Total Analysis Systems (µTAS). Two basic approaches can be identified, one being a stationary system with cycling temperature, the other being a flow system with three zones at different temperatures.

Stationary systems cycle the temperature of the chamber in order to modify the temperature of the PCR solution. They do not require a pumping system or other means of transfering the PCR sample. The flow-through systems typically have zones at three constant temperatures, between which the sample is moved and thus changes its temperature. While being faster than the stationary system, the flow-through system requires an implementation of a mechanism to transfer between the zones of different temperature. In either case a heater is integrated into the PCR system, so it is not economical to dispose of the device to avoid crosscontamination after performing only a single test.

A recent example of a stationary micro PCR method uses a planar chip device and the formation of a Virtual Reaction Chamber (VRC). The VRC is made by encapsulation of a water based sample in oil (Guttenberg, Z., et al., Lab Chip, 2005, 5, 308-317). As no solid cover or microchannels are required, the device fabrication consists only of deposition and patterning thin film heaters and temperature sensors on a suitable substrate. The respective device is however still too costly for a disposable system.

A further challenge occurring upon miniaturization is the risk of cross-contamination between samples. The safest way of avoiding such cross-contamination is the use of a disposable system. At the very least, the part of the device which comes into contact with the sample should be disposable. So far, many different systems have been proposed. These systems typically do not fulfil all the requirements listed above and they are relatively expensive. An approach with a disposable part made of a plastic sheet has been disclosed in U.S. Pat. No. 6,509,186. A set of wells is formed by hot embossing and the whole set is placed on top of heaters. This system employs a relatively complicated microfabrication process and the disposable plate needs to be customized. Therefore, there remains a need for a µPCR that is simple to manufacture, easy to operate, and economical enough to be disposable. The optional ability to be integrated into a complete µTAS system is highly desirable.

Accordingly it is an object of the present invention to provide an apparatus and a method for regulating the temperature of a chemical and/or biological sample which avoids these discussed disadvantages.

SUMMARY OF THE INVENTION

In one aspect the present invention provides an apparatus for regulating the temperature of a chemical and/or biological sample. The apparatus includes at least one temperature control module. The temperature control module includes a heater, a conductor of caloric, and a temperature sensor. The heater of the temperature control module is adapted to thermally communicate with a removable substrate, on which said chemical and/or biological sample is placed, via the conductor of caloric. The temperature sensor of the temperature control module is adapted to detect and control the temperature of the substrate via the conductor of caloric. The apparatus is designed such that the substrate is situated above said temperature control module to entirely cover said temperature control module.

In a further aspect the invention provides a method of regulating the temperature of a chemical and/or biological sample. The method includes providing an apparatus for regulating the temperature of a chemical and/or biological sample. The apparatus includes at least one temperature control module. The temperature control module includes a heater, a conductor of caloric, and a temperature sensor. The heater of the temperature control module is adapted to thermally communicate with a removable substrate, on which said chemical and/or biological sample is placed, via the conductor of caloric. The temperature sensor of the temperature control module is adapted to detect and control the temperature of the substrate via the conductor of caloric. The apparatus is designed such that the substrate is situated above said temperature control module to entirely cover said temperature control module. The method further includes providing a temperature value for heating the chemical and/or biological sample. The method also includes measuring the temperature of the conductor of caloric by means of the temperature sensor. The method further includes applying heat to said conductor of caloric as long as the measured temperature is below the provided temperature value, thereby heating said substrate and said chemical and/or biological sample.

BRIEF DESCRIPTION OF THE DRAWINGS

The invention will be better understood with reference to the detailed description when considered in conjunction with the non-limiting examples and the accompanying drawings, in which:

FIG. 3A depicts a schematic cross-section of an embodiment of a temperature control module of an apparatus of the invention, covered with a removable substrate (1), where on a sample (2) is located. The substrate (1) contacts a conductor of caloric (3), which is in turn in contact with a plurality of heaters (4) and a sensor (5).

FIG. 3B depicts a schematic cross-section of a further embodiment of a temperature control module. The sample is a liquid droplet, which includes an inner (6) and an outer phase (7). A substrate (1) contacts a concentric conductor of caloric (3), which is in turn in contact with a concentric heater (4) and a concentric sensor (5).

FIG. 4 shows schematically another embodiment of a temperature control module of the apparatus of the invention, seen from below. A heater (4) and a sensor (5) are each concentric, with the heater (4) surrounding the sensor (5). The conductor of caloric (3) includes two concentric parts, connected by a linker (10), as well as a rod-shaped part of a length (9).

FIG. 5 depicts arrangements of temperature control modules, where pairs of temperature control modules are opposing each other in the plane that is essentially parallel to the plane of the substrate, which is the plane of the substrate on which the sample is placed. All (FIG. 5A, FIG. 5C) or some pairs of the temperature control modules (FIG. 5B, FIG. 5D, FIG. 5E) may oppose each other as reversed images. FIG. 5F depicts an embodiment where pairs of temperature control modules are opposing each other in an angle that differs from 180°.

FIG. 6A depicts the results of a Finite Element Analysis (FEA) conducted by ANSYS software showing temperature uniformity above four temperature control modules with achieved temperatures of 55° C. (right), 72° C. (top), 72° C. (left) and 94° C. (bottom).

FIG. 6B shows an infrared image of the embodiment of an apparatus according to the present invention shown in FIG. 6A, including four heating elements soldered to a PCB.

FIG. 6C depicts the temperature profile along the line a . . . a' in FIG. 6B. The temperature variation above the temperature control modules is within ±0.5° C.

FIG. 9 depicts the fluorescence signal detected from an apparatus of the invention versus time during an exemplary PCR cycle. By subtracting the fluorescence signal at a temperature of 94° C. (second arrow) from the signal at a temperature of 72° C. (first arrow) real time data points can be plotted as shown in FIG. 10.

FIG. 10 depicts the fluorescence signal detected from an apparatus of the invention versus time during 50 PCR cycles. Real time data points were obtained by subtracting the fluorescence signal at a temperature of 94° C. (second arrow in FIG. 9) from the signal at a temperature of 72° C. (first arrow in FIG. 9). The cycle threshold value in the present example was about 25.

(cf. the Examples below). Measured data (lower curve, bold line) and sigmoid function (lower curve, fine line) are indistinguishable, demonstrating the purity of the obtained PCR product. The negative value of its derivation is shown in the upper curve.

Figure 14:
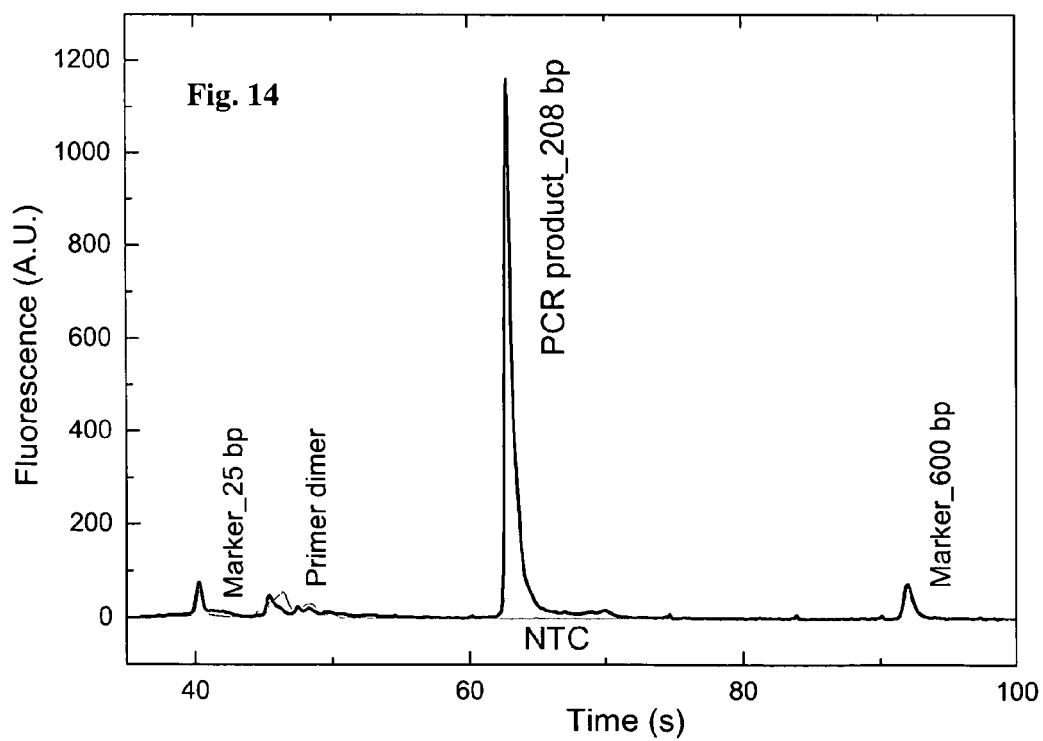

FIG. 14 depicts an elution profile of capillary electrophoresis. The results confirmed the purity of the PCR product.

DETAILED DESCRIPTION OF THE INVENTION

The present invention provides a method for regulating the temperature of a biological and/or chemical sample. The method is suitable for any sample, in particular a sample in liquid form such as e.g. a droplet (cf. below).

The sample may be of any origin. It may for instance, but not limited to, be derived from human or non-human animals, plants, bacteria, viruses, spores, fungi, or protozoa, or from organic or inorganic material of synthetic or biological origin. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule production sample, a protein preparation sample, a lipid preparation sample, a carbohydrate preparation sample, a space sample, an extraterrestrial sample or any combination thereof may be processed in the method. Where desired, a respective sample may have been preprocessed to any degree. As an illustrative example, a tissue sample may have been digested, homogenised or centrifuged prior to being used with the device of the present invention. The sample may furthermore have been prepared in form of a fluid, such as a solution. Examples include, but are not limited to, a solution or a slurry of a nucleotide, a polynucleotide, a nucleic acid, a peptide, a polypeptide, an amino acid, a protein, a synthetic polymer, a biochemical composition, an organic chemical composition, an inorganic chemical composition, a metal, a lipid, a carbohydrate, a combinatory chemistry product, a drug candidate molecule, a drug molecule, a drug metabolite or of any combinations thereof. Further examples include, but are not limited to, a suspension of a metal, a suspension of metal alloy, and a solution of a metal ion or any combination thereof, as well as a suspension of a cell, a virus, a microorganism, a pathogen, a radioactive compound or of any combinations thereof. It is understood that a sample may furthermore include any combination of the aforementioned examples.

Often, but not necessarily, the sample will include, or will be expected to include, target matter or a precursor thereof. The target matter may for instance be a cell or a molecule added to or included in the sample, and it may be desired to expose the target matter to heat. As another example, the target matter may be a compound known or theorized to be obtainable from a precursor compound by means of a chemical process that occurs upon increasing the temperature. In this case the sample may for instance include a solution of such precursor compound.

The target matter or precursor thereof may thus be of any nature. Examples include, but are not limited to, a nucleotide, an oligonucleotide, a polynucleotide, a nucleic acid, a peptide, a polypeptide, an amino acid, a protein, a synthetic polymer, a biochemical composition, an organic chemical composition, an inorganic chemical composition, a lipid, a carbohydrate, a combinatory chemistry product, a drug candidate molecule, a drug molecule, a drug metabolite, a cell, a virus, a microorganism or any combinations thereof. In embodiments where the target matter is for example a protein, a polypeptide, a peptide, a nucleic acid, a polynucleotide or an oligonucleotide, it may contain an affinity tag. Examples of affinity tags include, but are not limited to biotin, dinitrophenol or digoxigenin. Where the target matter is a protein, a polypeptide, or a peptide, further examples of an affinity tag include, but are not limited to, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly), maltose binding protein (MBP), the HSV epitope of the sequence Gln-Pro-Glu-Leu-Ala-Pro-Glu-Asp-Pro-Glu-Asp of herpes simplex virus glycoprotein D, the hemagglutinin (HA) epitope of the sequence Tyr-Pro-Tyr-Asp-Val-Pro-Asp-Tyr-Ala and the "myc" epitope of the transcription factor c-myc of the sequence Glu-Gln-Lys-Leu-Ile-Ser-Glu-Glu-Asp-Leu. Where the target matter is a nucleic acid, a polynucleotide or an oligonucleotide, an affinity tag may furthermore be an oligonucleotide tag. Such an oligonucleotide tag may for instance be used to hybridize to an immobilized oligonucleotide with a complementary sequence. A respective affinity tag may be located within or attached to any part of the target matter. As an illustrative example, it may be operably fused to the amino terminus or to the carboxy terminus of any of the aforementioned exemplary proteins.

The apparatus of the invention includes at least one temperature control module. In some embodiments the apparatus includes at least two temperature control modules. In yet further embodiments the apparatus includes a plurality of temperature control modules. Where the apparatus includes more than one temperature control module, they are typically thermally isolated from each other. Such isolation may be achieved by separating the temperature control modules by material that is a poor conductor of caloric, such as e.g. plastic, wood, glass, quartz, water, air or ceramic. In some embodiments thermal isolation by means of air may be advantageous, since no additional material may be introduced into the apparatus. Where desired, the apparatus may include further means of temperature control, such as a cooling module. Additionally or alternatively the temperature control module may include a cooler, which is for instance adapted to be able to thermally communicate with the conductor of caloric. In many embodiments where it is desired to handle a sample at temperature values that are about at or above room temperature, cooling the sample from a higher to a lower temperature value, e.g. from 94° C. to 55° C., can conveniently be achieved without a cooler. The apparatus of the invention can easily be designed to allow for heat emission from the conductor of caloric and the sample that provides fast cooling rates (cf. e.g. FIG. 8).

The temperature control module—or at least one of the temperature control modules of a plurality, and in some embodiments each of these temperature control modules—is based on a direct heating system in that it includes a heater and a temperature sensor. It furthermore includes a conductor of caloric. The heater is adapted to thermally communicate with the conductor of caloric, thus being able to heat the conductor of caloric. As an illustrative example, the heater may contact the conductor of caloric. Under the control of the temperature sensor the heater is thereby able to heat the conductor of caloric up to a desired temperature and/or keep the conductor of caloric at a desired temperature value. As also explained below, a reduction of the temperature value to which the heater is to heat the conductor of caloric, usually leads effectively to a decrease in the temperature of the same and may be defined as "cooling". Typically the temperature sensor is arranged to be able to communicate with the conductor of caloric, for example via direct contact. The conductor of caloric may be of any material that is able to conduct heat. The conductor of caloric may for example include a metal, a semiconductor, a diamond, a carbon nanotube or a fullerene compound. Examples of suitable metals include, but are not limited to, silver, copper, aluminium, zinc, gold, titanium, iron, lead, nickel, iridium and cadmium. Two illustrative examples of suitable semiconductors are silicon and germanium. Silver and silicon are two typical examples of a conductor of caloric with a conductivity of 410 $Wm^{-1}K^{-1}$ and 157 $Wm^{-1}K^{-1}$, respectively.

The heater, the sensor and the conductor of caloric may be of any shape and arranged in any orientation with respect to each other. In some embodiments the heater and the sensor are arranged on the same surface of the conductor of caloric (cf. also below). In some of these embodiments the heater and the sensor are arranged in direct vicinity to each other.

The apparatus of the invention is furthermore able to accommodate a removable substrate. Once a respective substrate is placed onto the apparatus of the invention, the apparatus may thus for instance be used as an incubator. As explained below, the apparatus may also be used as a reactor. The substrate, which the apparatus of the invention is adapted to be able to accommodate, may be of any desired material. Typically the material is able to conduct heat to at least a certain extent. Examples include, but are not limited to silicon, glass and plastic. It may furthermore be desired to select the substrate to be of a material that does not undergo an undesired reaction with the sample. It may likewise be desired to select the substrate to be of a material that does not interfere with, retard or prevent a reaction that is desired to occur in or with the sample. As an illustrative example, silicon (but not silicon oxide or silicon oxynitride) is known to inhibit a PCR reaction. The substrate may have any shape and geometry as long as it can be accommodated by the apparatus of the invention. It may for example be concave or convex rounded. In one embodiment the at least one surface is essentially flat. Where desired the substrate may include a cavity. Such a cavity may for instance be obtained by means of etching or laser drilling. In some embodiments the substrate may also be accommodated in a cavity of the apparatus.

It may be desired to select the material and/or shape of the substrate in order to convey a desired process or to prevent undesired reactions from occurring. In some embodiments it may for instance be desired to select a material that assists spreading of the sample to provide maximal contact with the surface and fast heating. In other embodiments it may be desired to provide e.g. a low wettability for the sample in order to prevent evaporation of liquid. The substrate may in some embodiments provide a surface the composition of which differs from the material composition of the remaining substrate. In some embodiments the surface of the substrate may be modified. Where for instance the sample is, or is included in, a hydrophilic, such as an aqueous, liquid, the substrate may be hydrophobic or oleophobic, where it is desired to minimize spreading and evaporation. A respective hydrophobic substrate may in some embodiments be selected from the group consisting of silicone, plastic, surface-modified glass, surface-modified quartz, surface modified metal, and composites thereof.

A surface modification is typically obtained by a treatment carried out to alter characteristics of a solid surface. Such a treatment may include various means, such as mechanical, thermal, electrical or chemical means. As an example, a surface of plastic materials can be rendered hydrophilic via treatment with dilute hydrochloric acid or dilute nitric acid. As another example, a polydimethylsiloxane (PDMS) surface can be rendered hydrophilic by an oxidation with oxygen or air plasma. The surface of a hydrophobic polymer, such as polymethylmethacrylate, polytetrafluorethylene, polyethylene terephthalate, and polycarbonate, may also be rendered hydrophilic by means of ionic radiation in the presence of a reactive gas, as described by Kim et al (2003 ECI Conference on Heat Exchanger Fouling and Cleaning: Fundamentals and Applications [2003], Vol. RP1, 107-114). Silicon may be rendered hydrophilic by dipping in $H_2O/H_2O_2/NH_4OH$. Furthermore, the surface properties of any hydrophobic surface can be rendered hydrophilic by coating with a hydrophilic polymer or by treatment with surfactants. Examples of a chemical surface treatment include, but are not limited to exposure to hexamethyldisilazane, trimethylchlorosilane, dimethyldichlorosilane, propyltrichlorosilane, tetraethoxysilane, glycidoxypropyltrimethoxy silane, 3-aminopropyl-triethoxysilane, 2-(3,4-epoxy cyclohexyl)ethyltrimethoxysilane, 3-(2,3-epoxy propoxyl)-propyltrimethoxysilane, polydimethylsiloxane (PDMS), γ-(3,4-epoxycyclohexyl) ethyl-trimethoxysilane, poly(methyl methacrylate) or a polymethacrylate co-polymer, urethane, polyurethane, fluoropolyacrylate, poly(methoxy polyethylene glycol methacrylate), poly-(dimethyl acrylamide), poly[N-(2-hydroxypropyl)methacrylamide] (PHPMA), α-phosphorylcholine-o-(N,N-diethyldithiocarbamyl)undecyl oligoDMAAm-oligo-SThlock co-oligomer (cf. e.g. Matsuda, T et al., Biomaterials, (2003), 24, 4517-4527), poly(3,4-epoxy-1-butene), 3,4-epoxy-cyclohexylmethylmethacrylate, 2,2-bis [4-(2,3-epoxy propoxy) phenyl] propane, 3,4-epoxy-cyclohexylmethylacrylate, (3',4'-epoxycyclohexylmethyl)-3,4-epoxy-cyclohexyl carboxylate, di-(3,4-epoxycyclohexylmethyl)adipate, bisphenol A (2,2-bis-(p-(2, 3-epoxy propoxy) phenyl) propane) or 2,3-epoxy-1-propanol.

On the substrate the chemical and/or biological sample is placed. Where the selected material of the substrate is a relatively poor conductor of heat (including a material with rather insulating porperties), the substrate may be of small thickness. As two illustrative examples, a glass slip or a thin pad of silicone rubber may be used. FIGS. 3A and 3B show two illustrative examples of a thin removable substrate. The removable substrate is able to thermally communicate with the conductor of caloric, once placed onto the apparatus of the invention. The heater is adapted to thermally communicate with the substrate via the conductor of caloric. Likewise, the temperature sensor is adapted to detect and control the temperature of the substrate via the conductor of caloric. Therefore, under the control of the temperature sensor the heater is able to heat the substrate up to a desired temperature and/or keep the substrate at a desired temperature value. In embodiments such as those depicted in FIGS. 3A and 3B, a glass or rubber substrate is suitable to transfer the heat from the conductor of caloric to the sample, even though it is a poor conductor of heat. In some embodiment selecting a substrate of low thermal conductivity may even be advantageous, since this may provide a further means of thermally isolating one temperature control element from another, in addition to e.g. a thermal isolation.

The apparatus of the invention is designed in such a way that the removable substrate is situated above the temperature control module. The terms "above" and "below" as used herein, refer to a position, where the apparatus of the present invention is held in such a way that the substrate may be placed on the apparatus and once placed thereon can be secured solely by the force of gravitation. In this position the apparatus can usually be placed onto a flat surface. In some embodiments in this position the heater is located below the conductor of caloric. In some embodiments both the heater and the sensor are located below the conductor of caloric.

In some embodiments the heater includes a surface that is arranged essentially parallel to the plane of the removable substrate, on which plane of the substrate the sample is placed. In some embodiments the heater includes a surface that is arranged essentially parallel to the plane of the substrate, on which plane of the substrate the sample is placed. In some embodiments both the heater and the sensor include a surface that is arranged essentially parallel to the plane of the substrate, on which plane of the substrate the sample is placed. In some of these embodiments the heater and the sensor each comprise a surface arranged in a common plane. This common plane is thus essentially parallel to the plane of the substrate, on which plane of the substrate the sample is placed. In any of these embodiments the heater, the sensor or both may be located below the conductor of caloric.

In any of these embodiments, in particular where the heater and the sensor each comprise a surface arranged in a common plane, the heater or the sensor may be concentric. In some embodiments both the heater and the sensor are concentric. One or both of them, or parts thereof, may for instance have the shape of a hollow circle, a hollow rectangle, a hollow triangle, a hollow square, or any hollow or any oligoedron (cf. e.g. FIG. 5 for examples). Temperature control modules that contain elements of square shape have for example been disclosed by Guttenberg et. al. (cf. below). In one of these embodiments both the heater and the sensor are concentric and the heater surrounds the sensor. In another embodiment both the heater and the sensor are concentric and the sensor surrounds the heater. In an embodiment, which is depicted in a cross-section in FIG. 3B, both the heater and the sensor are concentric and arranged under a concentric conductor of caloric. It should be noted that in the depicted embodiment the heater, the sensor and the conductor of caloric include a central hollow area, so that they each appear as respective pairs.

In some embodiments the conductor of caloric, or a part thereof, is of a shape that is adapted to match the shape of the sensor and/or the heater. Where the sensor and the heater are for instance of a square or round concentric shape with a hollow centre, the conductor of caloric may posses a corresponding square or round concentric shape with a hollow centre. Where a part of the conductor of caloric is adapted to match the shape of the sensor and/or the heater, it may include additional other parts of any desired shape. As an illustrative example, it may include a rod-shaped part. Where for instance the part of the conductor of caloric, which is adapted to match the shape of the sensor and/or the heater, is of circular profile, the conductor of caloric may be of donut shape. FIG. 4 depicts an exemplary embodiment, in which the conductor of caloric includes two concentric parts, which are connected by a linker. The inner of these concentric parts is in direct contact with a concentric sensor and a concentric heater, the latter surrounding the sensor. The conductor of caloric furthermore includes a rod-shaped part. It is thus of double donut shape. Thermal conductance is given by the material of conductor of caloric, the length of the rod-shaped part, and the cross-section of the concentric parts. Thermal capacitance is given by the double donut volume (cf. FIG. 4) with the volume of the sample.

Figure 1:
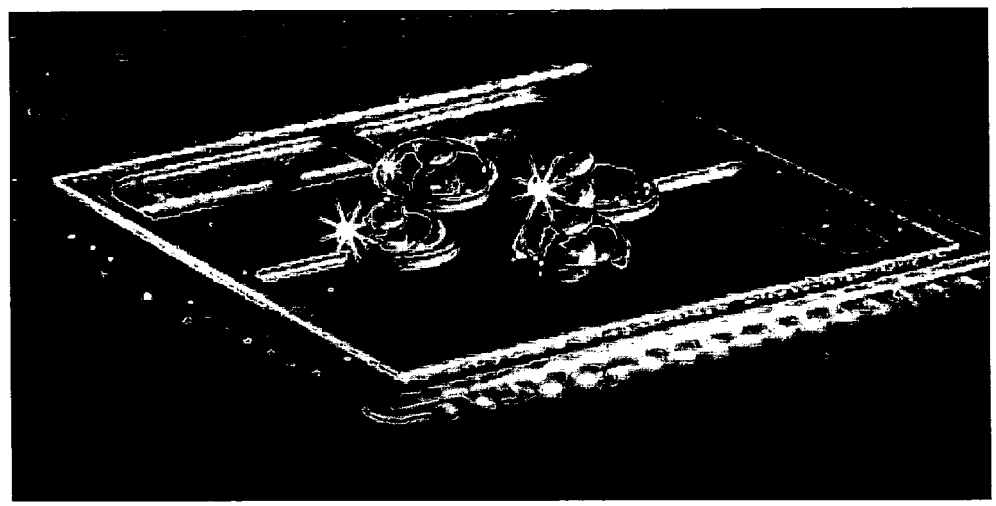
FIG. 1 depicts a photograph of an embodiment of an apparatus of the invention. The temperature control modules are soldered to a Printed Circuit Board (PCB). Situated thereabove is a square glass slide as a substrate. Samples are placed on the substrate in the form of liquid droplets.
Figure 2:
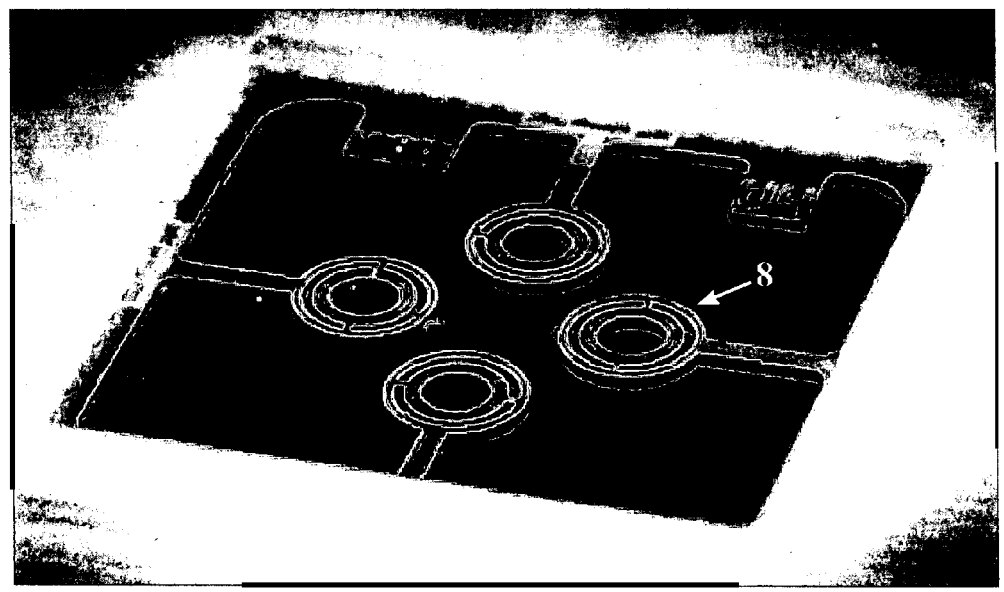
FIG. 2 is a further photograph of the apparatus of the invention as depicted in FIG. 1. The temperature control modules (8) are soldered to a Printed Circuit Board (PCB). A removable substrate can be placed onto the apparatus. A respective substrate (cf. also FIG. 1) entirely covers the temperature control modules.

In embodiments where the apparatus includes more than one temperature control module, the temperature control modules may each include a surface arranged in a common plane. This common plane may be essentially parallel to the plane of the substrate, on which plane of the substrate the sample is placed. In some of these embodiments, in particular where the heating elements are of identical dimensions, the temperature control modules as a whole may also be arranged to be located in a common plane. In any of these embodiments—for instance where at least two temperature control modules each include a surface arranged in a common plane—the temperature control modules may be opposing each other in the respective plane, e.g. the plane which is essentially parallel to the plane of the substrate. As illustrated in FIG. 5, the apparatus may for example include two, three, four, five or more pairs of temperature control modules. The two temperature control modules of each pair may oppose each other in the plane that is essentially parallel to the respective plane of the substrate (i.e. the plane on which the sample is placed). An example of a respective arrangement is for instance depicted in FIG. 2 (cf. also FIG. 5). FIG. 1 depicts a corresponding arrangement with a glass cover slid as a substrate and samples placed thereon. The samples shown in FIG. 1 are water based droplets each with a volume of 1 μl and placed directly above the temperature control modules, which are located on the other side of the substrate. The water droplets in the shown embodiment are covered with 5 μl of mineral oil. As e.g. illustrated in FIG. 5E and FIG. 5F, the temperature control elements may be arranged in a row, analogous e.g. to the arrangement of wells on a multi-well plate. Several such rows can be combined to provide an apparatus with e.g. 32, 48 or 96 individually controllable temperature control elements. Accordingly, the apparatus of the present invention may be used to carry out individual biological and/or chemical reactions (cf. also below) in a multi-well format, thereby significantly advancing the current state of the art, which only allows applying a common temperature profile to all samples of a multiplexing assay.

The apparatus of the present invention is further designed in such a way that the removable substrate entirely covers the temperature control module. In embodiments where the apparatus includes more than one temperature control module, the removable substrate may entirely cover all the temperature control modules of the apparatus.

The present invention further provides a method of regulating the temperature of a chemical and/or biological sample, for instance a sample that is included in a liquid droplet. The method includes providing an apparatus as described above. The method further includes providing a predefined temperature value for heating the chemical and/or biological sample. This temperature value may for example be stored in an external device communicating with the heater. The method also includes measuring the temperature of the conductor of caloric by means of the temperature sensor. The measured temperature value may for instance be communicated to an external device, where the measured temperature is compared to the predefined temperature value. Furthermore the method includes applying heat to the conductor of caloric as long as the measured temperature is below the provided temperature value by means of the heater. Thereby the substrate and the chemical and/or biological sample are heated.

Furthermore, more than one predefined temperature value may be selected and a period of time may be associated with each of the respective temperature values. Accordingly a time schedule with predefined heating and non-heating intervals of any desired length may be set in advance and subsequently be carried out using the method of the invention. As an illustrative example, a PCR cycling process as illustrated above (cf. also the examples below) may be carried out using the method of the present invention (see also FIG. 8). It should be understood that an interval may also be selected, during which the temperature gradually increases or decreases. This may for instance be achieved by gradually increasing or decreasing the predefined temperature value (and accordingly the heating to occur) with time.

As indicated above, in some embodiments the apparatus of the invention includes more than one temperature control module. Accordingly, a respective apparatus may be used in the method of the invention. In some of these embodiments the temperature control modules of the apparatus are thermally isolated from each other (cf. above). In such embodiments individual temperature values may be provided for heating the chemical and/or biological sample at a respective temperature control module of the apparatus. Accordingly the method of the invention may in such embodiments include providing an individual temperature value for each temperature control module. As explained above, this temperature value is typically set for heating a chemical and/or biological sample, which may be placed on a substrate above the respective temperature control module. Thus a plurality of samples may be selected to be heated independently, simultaneously, or within overlapping time frames using the same apparatus. For any desired number of these samples, for instance for each and every sample, there may thus be provided a respective set of heating and/or non-heating intervals.

In embodiments where an apparatus is used that includes at least two temperature control modules, which are thermally isolated from each other, the temperature of the conductor of caloric of each temperature control module may furthermore be measured individually. This measurement is generally carried out by means of the temperature sensor of the respective temperature control module. In such embodiments the method of the invention may also include individually applying heat to the conductor of caloric of each temperature control module as long as the measured temperature is below the provided temperature value. Thereby each substrate, and as a consequence a chemical and/or biological sample placed thereon, is heated individually.

Accordingly, for each temperature control module more than one predefined temperature value may be selected independently from any other temperature control module, and an individual period of time may be associated with each of the respective temperature values at each temperature control module. Accordingly an individual time schedule with predefined heating and non-heating intervals of any desired length may be performed at each temperature control module using the method of the invention. As an illustrative example, independent PCR cycling processes may be carried out on a plurality of temperature control modules on the same apparatus.

In some embodiments of the method of the invention providing the apparatus includes providing a substrate. The substrate, which can be accommodated by the apparatus (supra) is disposed above the temperature control module, so that it entirely cover it. Providing the apparatus may also include providing a chemical and/or biological sample and disposing it onto the substrate. The sample may be provided by any means. As an illustrative example, where the sample is a liquid droplet, it may be dispensed onto the substrate by a pipette or an automatic dispenser.

As indicated above, the sample may be a liquid droplet or included therein. In some embodiments the method of the invention includes providing a respective liquid droplet. The liquid droplet may be of any desired volume as long as it can be placed on the substrate. Accordingly the heating modules may be selected to be of a corresponding size. A temperature control module that is designed to heat a liquid droplet may for instance be of the size of a few millimetres or on the micro- or nanoscale. Where desired, the apparatus of the invention, even in embodiments where it includes a large number of temperature control modules, may thus be a portable apparatus.

The liquid droplet may include other matter, such as for instance magnetically attractable matter. As an illustrative example, in some embodiments magnetically attractable particles may be included in the liquid droplet. Such particles may be able to attract target matter. In some embodiments the magnetic particles can be functionalised with specific affinity for target matter and capturing target matter, therefore acting as a binding means.

In some embodiments the liquid droplet includes an inner phase and an outer phase, where the outer phase is for instance surrounding the inner phase as a film. In such embodiments typically the liquid of the outer phase is immiscible with the liquid of the inner phase. Any liquid may be used for the respective phase. Where a droplet contains two immiscible phases, one phase is typically formed by a polar liquid (such as e.g. water, ethanol, acetone, N,N-dimethyl-formamide or nitromethane), while the other phase is formed by a non-polar liquid (such as e.g. benzene, hexane, dioxane, tetrahydrofuran or diethyl ether).

The sample may be mixed with further matter, for example dissolved or suspended therein, or provided together with it in e.g. the same liquid. As an illustrative example an aqueous sample may include one or more buffer compounds. Numerous buffer compounds are used in the art and may be used to carry out the various processes described herein. Examples of buffers include, but are not limited to, solutions of salts of phosphate, carbonate, succinate, carbonate, citrate, acetate, formate, barbiturate, oxalate, lactate, phthalate, maleate, cacodylate, borate, N-(2-acetamido)-2-amino-ethanesulfonate (also called (ACES), N-(2-hydroxyethyl)-piperazine-N'-2-ethanesulfonic acid (also called HEPES), 4-(2-hydroxyethyl)-1-piperazine-propanesulfonic acid (also called HEPPS), piperazine-1,4-bis(2-ethanesulfonic acid) (also called PIPES), (2-[Tris(hydroxymethyl)-methylamino]-1-ethansulfonic acid (also called TES), 2-cyclohexylamino-ethansulfonic acid (also called CHES) and N-(2-acetamido)-iminodiacetate (also called ADA). Any counter ion may be used in these salts; ammonium, sodium, and potassium may serve as illustrative examples. Further examples of buffers include, but are not limited to, triethanolamine, diethanolamine, ethylamine, triethylamine, glycine, glycylglycine, histidine, tris(hydroxymethyl)-aminomethane (also called TRIS), bis-(2-hydroxyethyl)-imino-tris(hydroxymethyl) methane (also called BIS-TRIS), and N-[Tris(hydroxymethyl)-methyl]-glycine (also called TRICINE), to name a few. The buffers may be aqueous solutions of such buffer compounds or solutions in a suitable polar organic solvent.

Further examples of matter included in a sample, e.g. in a phase of a liquid droplet, include, but are not limited to, reagents, catalysts and reactants, for carrying out a chemical or biological process. As an illustrative example, salts, substrates or detergents may be added in order to maintain cells or proteins in an intact state. As a further illustrative example, chelating compounds may be required, for instance to protect organisms from traces of otherwise toxic salts or to increase the yield of a chemical reaction. As yet a further illustrative example, protease inhibitors may need to be added in order to maintain proteins in an intact state. A further example of a possible additive to a sample includes magnetically attractable particles (see above). It is understood from the above that such additional matter may be included in a liquid droplet. Where the liquid droplet includes more than one phase, such matter may for instance be included in the same phase as the sample or in a different phase.

Heating the biological sample may in some embodiments initiate, resume or cause an acceleration of a process on the same. Therefore the method of heating the respective sample includes in some embodiments carrying out a biological and/or chemical process. An illustrative example of a respective process is a chemical reaction. Examples of a chemical reaction include, but are not limited to, a chemical synthesis, a chemical degradation, an enzymatic synthesis, an enzymatic degradation, a chemical modification, an enzymatic modification, an interaction with a binding molecule, and any combination thereof. Examples of an enzymatic synthesis include, but are not limited to a protein synthesis, a nucleic acid synthesis, a peptide synthesis, a synthesis of a pharmaceutical compound, and any combination thereof. Additional devices may be used to assist or monitor the process. The implementation of diverse optical detection systems, e.g. photodiodes (PD), photo multiplier tubes (PMT), photon counting modules (PCM), spectrometers, and charge-coupled devices (CCDs) for instance allows monitoring such biochemical reactions in parallel and real-time.

Figure 12:
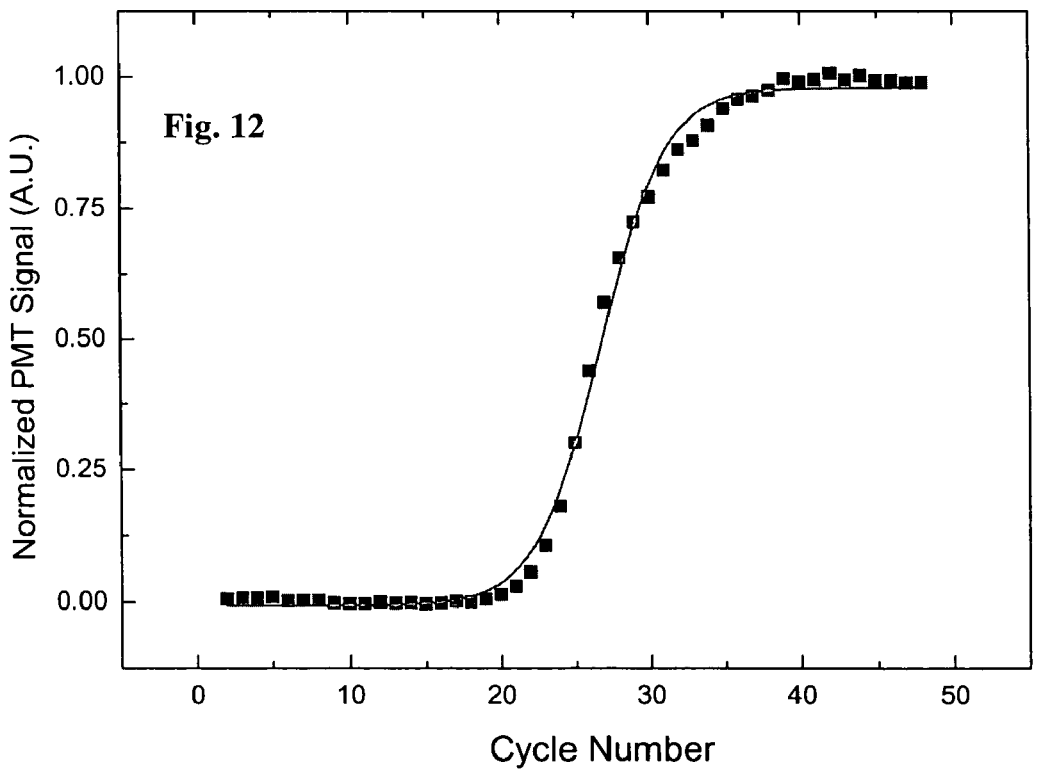
FIG. 12 depicts a plot of the normalized fluorescence signal (■) vs. the cycle number for 10 000 copies, fitted with a sigmoid function (line).

As an illustrative example, the sample may include a nucleic acid molecule and heating the chemical and/or biological sample may comprise the polymerase chain reaction ('PCR', see also above). Real time detection provides an amplification plot depicting the fluorescence signal versus reaction time expressed as cycle numbers (see FIG. 12). An increase in fluorescence above the baseline indicates the detection of accumulating amplification product. Where a fixed fluorescence threshold is set above the baseline, the fluorescence signal thus passes this threshold at a certain time point. As time is expressed in terms of cycle numbers, a so-called Cycle Threshold ($C_T$) number (or value) is obtained. The smaller this number, the further to the left is a respective fluorescence curve located in the amplification plot and the higher the concentration of the starting template. The higher $C_T$ number corresponds to the lower concentration of the starting template.

The term "nucleic acid molecule" as used herein refers to any nucleic acid in any possible configuration, such as single stranded, double stranded or a combination thereof. Nucleic acids include for instance DNA molecules (e.g., cDNA or genomic DNA), RNA molecules (e.g., mRNA), analogues of the DNA or RNA generated using nucleotide analogues or using nucleic acid chemistry, and PNA (protein nucleic acids). DNA or RNA may be of genomic or synthetic origin and may be single or double stranded. In the present method of the invention typically, but not necessarily, an RNA or a DNA molecule will be used. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label (cf. above).

Many nucleotide analogues are known and can be used in nucleic acids and oligonucleotides used in the present method of the invention. A nucleotide analogue is a nucleotide containing a modification at for instance the base, sugar, or phosphate moieties. As an illustrative example, a substitution of 2'-OH residues of siRNA with 2'F., 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

The apparatus and method of the invention may in some embodiments be used to determine the thermal stability of target matter or the thermal stability of a binding complex between target matter and other matter.

The method of the invention may be combined with such analytical and preparative methods, as for instance isoelectric focusing, chromatography methods, electrochromatographic, electrokinetic chromatography and electrophoretic methods. Examples of electrophoretic methods are for instance free flow electrophoresis (FFE), polyacrylamide gel electrophoresis (PAGE), capillary zone or capillary gel electrophoresis. The combination with such methods may include a common substrate. As an example, a separation of proteins may be performed on a small surface, e.g. a micro chip, for instance by isoelectric focussing. The respective surface may then be heated using the apparatus and method of the present invention, for instance to carry out a chemical and/or biological reaction.

In order that the invention may be readily understood and put into practical effect, particular embodiments will now be described by way of the following non-limiting examples.

EXAMPLES

Finite Element Analysis

A simple donut structure consisting of four heaters each connected by a beam to the substrate, as well as a double donut shape with the heater and sensor located at the inner donut (FIG. 4), were modeled by the Finite Element Analysis (FEA) software, ANSYS version 9.0. Elements SHELL-57 with real constants of 450 μm for silicon and 170 μm for glass were used. Typical boundary conditions for the model were set at the chip perimeter to 25° C. and adequate amplitude of heat flux was dissipated in all four donut shapes to set their temperatures at 94° C., 72° C. and 55° C.

For the simple donut structure the greatest thermal gradient was found to be along the beam axis. There was also a thermal gradient along the donut shape causing a relatively high temperature nonuniformity of 1° C. within the area of interest.

The two donuts of the double donut shape are connected by two beams with thermal conductivities of at least half that of the inner donut. It results in temperature uniformity within the inner donut. Simulation results of a double donut structure are shown in FIG. 6, demonstrating achieved temperature uniformity. The heat was dissipated almost entirely via the cantilevers, supporting our expectation that the cross talk between zones will be minimal. This design allows control temperature of all four areas independently from each other and thus we could run four different PCR protocols simultaneously. The chip used to obtain the apparatus was designed with a bonding pad configuration identical to a standard LCC-68 socket, so that it could be clamped into a conventional testing socket to determine device thermal parameters. Since our device thickness was only 0.45 mm as compared to the standard LCC chip which has a thickness of about 3 mm, a plastic frame was added on the top of the chip to compensate for its smaller thickness in order to get good electrical connection.

Fabrication

The basic substrate for device fabrication was a conventional 4" silicon wafer. A 1 μm layer of silicon oxide was deposited by Plasma Enhanced Chemical Vapor Deposition (PECVD). The $SiO_2$ film serves as an electrical insulator between the silicon and the subsequent metal film. A 250 nm gold layer with a thin chrome adhesion layer was deposited by e-beam evaporation with a total sheet resistance of 0.11Ω/□. The Au/Cr layer was lithographically patterned using 2 μm thick AZ 7220 positive photoresist to form the heater, sensor, electrical lead outs, and contact pads.

Both metals were etched by conventional etching solutions: gold by $KI/I_2$ and chrome by $(NH_4)_2Ce(NO_3)_6$ based solutions. After etching of the metal sandwich, the photoresist was stripped by acetone and the second lithography step was performed using 10 μm thick AZ4620 photoresist. The thick photoresist was chosen to serve as a mask for silicon etching by Deep Reaction Ion Etching (DRIE) through the entire thickness of the silicon wafer. Besides preventing silicon from being etched by the DRIE, the photoresist also protected the gold lines. Silicon oxide was first etched by 7:1 Buffered Oxide Etch (BOE) to expose bare silicon and it was followed by DRIE (Bosch process, cf. e.g. U.S. Pat. No. 5,498,312). As the chip scribe lines were also patterned, the DRIE process produced individual chips and eliminated the need for dicing of relatively fragile MEMS structures. The last process step was the individual chip cleaning by Piranha solution ($H_2SO_4$/$H_2O_2$), rinsing by de-ionized (DI) water and drying by means of a flow of nitrogen gas.

Apparatus Characterization

The electrical parameters of fabricated devices were determined by probing the device at the probe station (Cascade Microtech, Inc.) at different temperatures. The resistors' values were measured by an Agilent 4156C Semiconductor Parameter Analyzer.

The resistance value R of a resister versus temperature difference ΔT can be described by a simplified equation:

$$R = R_0(1 + \alpha \Delta T)$$

Where $R_0$ is the resistor value at nominal temperature and α is the material Temperature Coefficient of Resistance (TCR). Both parameters were derived from the measured data (see Table 1). Once the RO and values were calculated, the chips were soldered to the PCB so that we could measure their thermal parameters.

The thermal behaviour of any system is described by the differential heat balance equation:

$$H d\Delta T/dt + G\Delta T = \Delta P, \quad (2)$$

where H is the thermal capacitance and G is the thermal conductance of the system, ΔT is the temperature change, t is time and ΔP is the change of dissipated power within the system.

Previously, a pulse method to derive thermal parameters of bolometers for infrared detection was published (Neuzil, P, Mei, T., Applied Physics Letters, 2002, 80, 1838-1840). Since bolometers exhibit behaviour similar to PCR devices, an identical testing method was used. The sensor under evaluation together with three external resistors formed a balanced Wheatstone bridge. It was powered by pulses with durations of 1 ms and voltage amplitude of 5V with a repetition of 1 pulse per second.

A DC voltage signal with amplitude between 0V and 1V was superposed onto the pulses. The thermal capacitance H of the device is calculated from the derivative of temperature with respect to time. The temperature increase above ambient due to the applied DC voltage is a function of thermal conductance G. Obtained values of H and G were verified by direct measurement of the system time constant τ (equal to H/G). All measured and calculated electrical and thermal parameters are listed in Table I.

TABLE I

Electrical and thermal parameters of the PCR chamber. All values were measured at an ambient temperature of 23° C.

| | |
|---|---|
| Sensor resistance | 320 Ω |
| Heater resistance | 110 Ω |
| Sensor TCR | 0.33%/K |
| Sensor sheet resistance | 0.11 Ω/□ |
| Unit heat conductance | 4.40 mW/K |
| Unit heat capacitance | 6.60 mJ/K |
| PCR thermal time constant | 1.74 s |

Temperature Distribution

In order to electrically and mechanically connect the chip, we soldered it to a Printed Circuit Board (PCB) using a technique similar to flip-chip bonding. The solder formed the electrical and mechanical connection between the PCR device and the PCB (see FIG. 2).

The apparatus was connected to the temperature control electronics (see FIG. 7) as described below. The temperatures of the individual heaters was set approximately to 65° C., 85° C., and 94° C. and Infrared (IR) images at wavelengths from 8 to 12 μm were captured. The camera temperature resolution was 0.1 K of the Noise Equivalent Temperature Difference (see FIG. 6). As shown in FIG. 6, the temperature variation across the heaters is less than 1° C. and thus the device is well-suited to perform e.g. a PCR operation.

Control System

Temperature above ambient is controlled by modulating heating power. We have employed the Pulse-Width Modulation (PWM) principle. It controls an average dissipated power by modulating the duty cycle of power pulses significantly shorter than the system time constant.

The PWM is digital and it is easy to implement with a LabVIEW Data Acquisition (DAQ) card controlled from a Personal Computer (PC). A value of a temperature sensor at the chip was used for a closed feedback mode. The Proportional Integrated Derivative (PID) method was implemented to achieve fast heating. The maximum current supplied from the LabVIEW card 6014-E is only 8.5 mA of current which is not enough for the PCR chip heating to desired temperature. The card was then interfaced with the PCR chip by an integrated circuit IR 2121 (International Rectifiers, Inc.), a high speed MOSFET/IGBT driver. Its output is capable of supplying an electrical current as high as 1 A with a frequency of pulses of up to 10 kHz, capable of powering the PCR chip.

Figure 7:
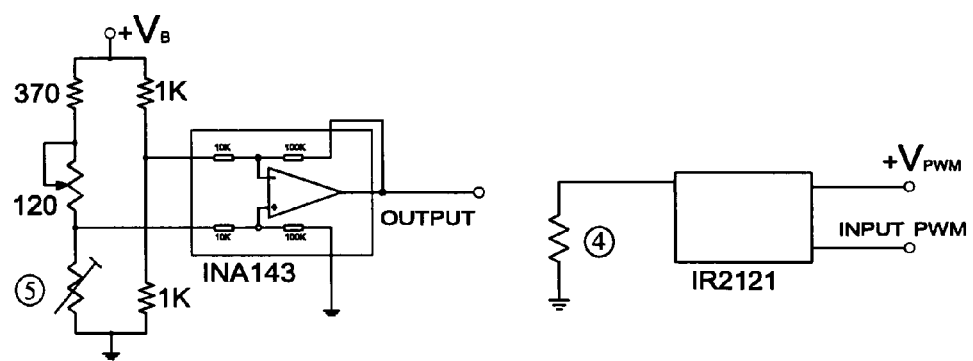
FIG. 7 depicts an electrical schematic of a single channel temperature control module of an apparatus of the invention. The heater (4) and the sensor (5) are part of the temperature control module, while the other devices are placed at the external Printed Circuit Board.

The temperature sensor together with two fixed and one adjustable resistor formed a Wheatstone bridge. Its outputs were connected to an INA143US (Burr-Brown, Inc.) differential amplifier with a fixed gain of 10. Its output was linked with LabView software by the same card as the one which controlled the IR 2121. The complete schematic of one channel placed at a PCB board is shown in FIG. 7. The complete PCB consists of four individual channels to four PCRs in parallel.

The apparatus was calibrated to a temperature precision of better than 0.5° C. The device calibration was performed in a temperature controlled bath filled with Fluorinert™ 77. Its temperature was measured by temperature sensors TSic™

(IST-AG, Watwill, Switzerland) calibrated with a precision of 0.1° C. in the range from 50° C. to 100° C., soldered at the PCB next to the PCR device.

The output values from all four channels were stored in a LabVIEW setup file and used for the feedback measurement. The microscope glass cover slip was placed on the PCR chip. A Virtual Reaction Chamber (VRC) with a volume of 1 μL and 5 μL of sample and oil was dispensed above the heaters (see FIG. 1). The above procedure precisely verified the temperature of the heater but not of the PCR sample itself which could be different. The sample temperature was determined by melting curve analysis (Rutledge, R. G., Nucleid Acids Research (Methods on-line) 2004, 32, e178), as described below. The sample temperature was found to be two degrees lower than the temperature of the heater at 94° C. and the setup file was corrected accordingly.

Thermal Cycling

Figure 8:
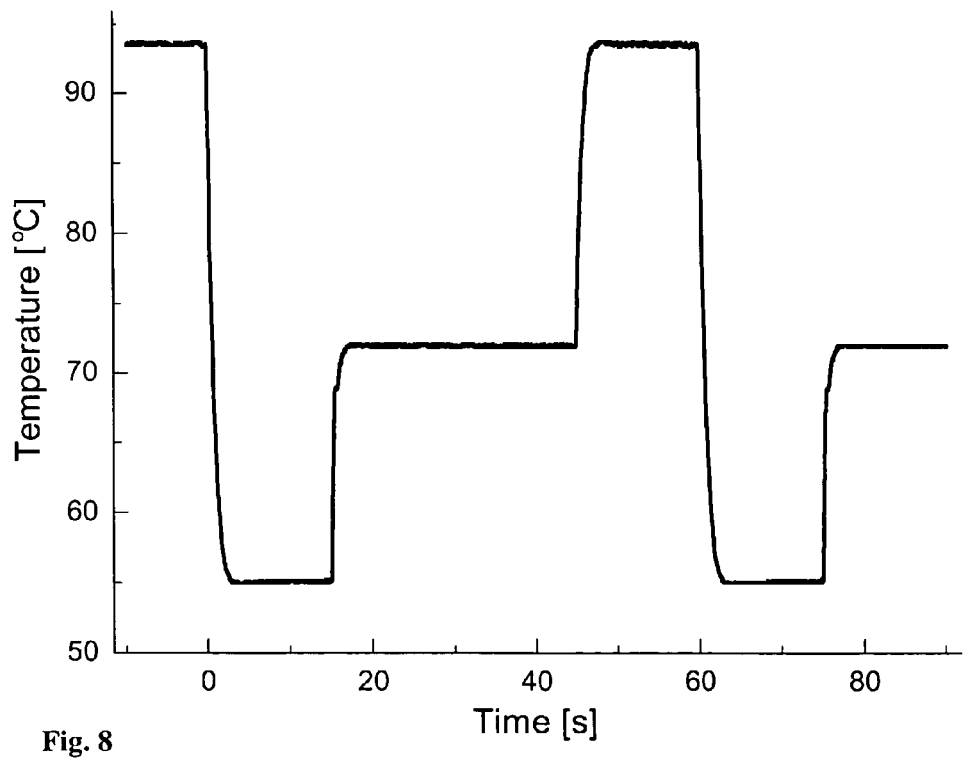
FIG. 8 depicts a temperature/time profile during PCR using the apparatus and method of the present invention. It requires only 2 seconds for a temperature decrease from 94° C. to 54° C., while heating is significantly faster, as it is controlled by a PID system.

The self-calibration procedure was performed to optimize PID values of the controller in order to achieve a fast heating response while the cooling rate was determined by the thermal time constant and surrounding temperature. From the thermal parameters listed in Table I it is expected that the device cooling time should be between one and two seconds as the temperature change from 94° C. to 55° C. is about 56% of the temperature difference between 94° C. and ambient room temperature of 25° C. That would give the system a fast cooling rate between $-20\,Ks^{-1}$ to $-40\,Ks^{-1}$, greatly exceeding the required minimal rate of $-5\,Ks^{-1}$. The achieved PCR thermal profile is shown in FIG. 8 with 15 seconds for denaturating (94° C.), 15 seconds for annealing (55° C.) and 30 seconds for elongation (72° C.).

Fluorescence Detection

A mercury lamp with a FITC excitation/detection cube was employed that corresponded to the systems used earlier (Dasgupta, P. K., et al., Anal. Chim. Acta, 2003, 500, 337-364; Cady, N. C., et al., Sensors and Actuators B: Chemical, 2005, 107, 332-341), with the fluorescence response detected by a Photo Multiplier Tube (PMT) (Hamamatsu H5784-20) with the gain set to about $5\times10^4$. The PCR chip was placed under a Zeiss Axiotech Vario microscope mounted on an optical table. The whole measurement setup was covered with a black cloth in order to suppress the amount of ambient light entering the PMT in order to increase the optical detection limit. An oscilloscope measured and stored the value of the PMT signal amplitude.

Apparatus Testing

(a) Surface Preparation

As described by Guttenberg et. al (Lab Chip, 2005, 5, 308-317), the glass surface for the VRC system has to be hydrophobic as well as oleophobic.

Several different fluorinated silane solutions and preparation methods were tested. The subsequently selected coating consisted of cleaning the glass in a 3:1 $H_2SO_4/H_2O_2$ mixture, followed by a DI water wash. The glass was then placed in a vacuum oven (YES-15E by Yield Engineering, Inc.) at room temperature together with a beaker containing 1 mL of a silane [(heptadecafluoro-1,1,2,2-tetrahydrodecyl) trimethoxysilane] by Gelest, Inc. The oven was then evacuated to reach a residual pressure of below 1 Torr and the oven temperature was raised to 150° C. while pumping was continued. Silane was vaporized and reacted with the glass surface. After 2 to 5 hours, the pumping was stopped, the oven was vented with nitrogen and glass slides were removed from the oven. Results of surface treatment were verified by the contact angle method using Contact Angle System (Model OCA 30 made by Dataphysics GmbH). The contact angle of a water droplet was 110 degrees while a mineral oil (Sigma Inc.) droplet had a contact angle of 70 degrees.

(b) Sample Preparation

As a test vehicle, 940 template copies of a 208 base pair fragment (Maxim Biotech, Inc.) of the gene encoding for human glycerinaldehyde 3-phosphate dehydrogenase (GAPDH) were used. 5'-CTCATTTCCTGGTATGA-CAACGA-3' (SEQ ID No: 1) was used as a forward primer and 5'-GTCTACATGGCAACTGTGAGGAG-3' (SEQ ID No: 2; Research Biolabs, Inc.) as a reverse primer. The PCR mixture was prepared in a 50 μl stock solution as recommended by the manufacturer (Qiagen, Inc.) with two exceptions: SYBR Green (Invitrogen, Inc.) was diluted to a final concentration of 1:10 000 and bovine serum albumin (Carl Roth, Inc.) was added in a final concentration of 1%.

(c) Real-Time PCR Results

The PCR stock solution prepared as described above was divided into two parts, where 1 μl was used for the PCR chip and the remainder was used in a conventional thermocycler (MJ Research, Inc.) as a reference. For both experiments the PCR mixture was covered by 5 μL of mineral oil (Sigma, Inc.). Thermocycling conditions were as follows: 5 minutes at 94° C. (initial denaturating), followed by 50 cycles of 1 minute at 94° C. (denaturating), 1 minute at 58° C. (annealing) and 1 minute at 72° C. (extension) with a final step of 10 minutes at 72° C. One minute per thermal step of the PCR cycle is longer than normal. However, it assures that the system reaches thermal equilibrium and the enzymatic reaction is completed during each step. This is more important at this point of time than the optimization of each step to render the PCR system fast.

For melting curve analysis (Rutledge, R. G., supra) the sample was cooled down to 65° C. for 1 minute after which the temperature was continuously raised to 95° C. with a heating rate of 0.01 $Ks^{-1}$. During the operation, both the fluorescence signal (see FIG. 9, FIG. 10) as well as the temperature sensor value was recorded simultaneously. The next step was the calculation of an average value of the fluorescence signal during the end of the extension phase at 72° C. In order to extract the fluorescence output signal from the PCR cycles, a short program was prepared using Fortran. The program input parameters were the centre of the first data block shown by a first arrow in FIG. 9, length of the data interval and the number of intervals. The program then averaged the signal from the interval and associated it with a cycle number for all 50 cycles. The same procedure was repeated for the fluorescence signal at 94° C. (indicated by the second arrow in FIG. 9) in order to obtain a baseline signal to be subtracted from the PCR output signal at 72° C. The subtracted data set was approximated with a sigmoid function:

$$y = \frac{A_1}{1 + \exp\left(\frac{x - x_0}{k}\right)} + A_2, \tag{3}$$

where $A_1$, $A_2$ are normalization constants, parameter xo represents the location of the inflexion point and k determines the maximum slope at that point.

Figure 11:
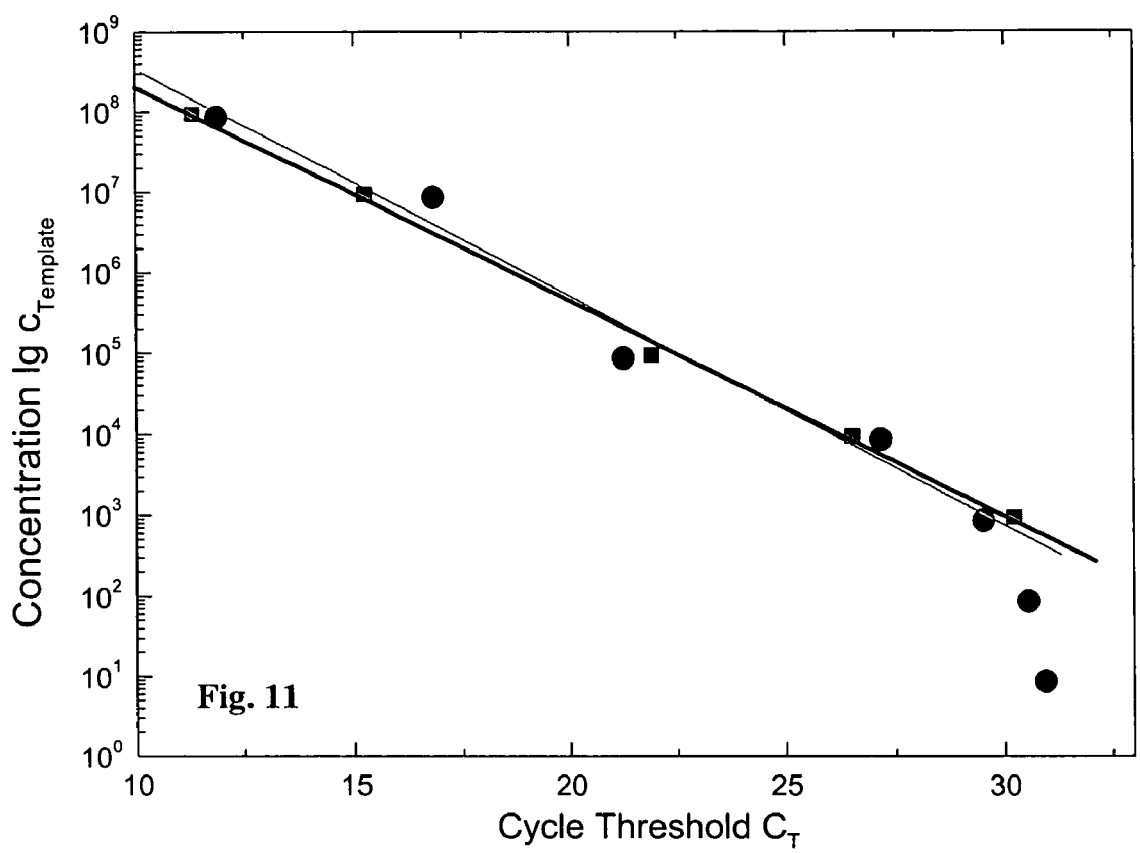
FIG. 11 shows a comparison of a micro PCR slope using the apparatus and method of the invention (■, bold line) and results obtained with a commercial system by MJ Research, Inc. (●, thin line).

The PCR protocol was run with different concentrations of template copies varied from 10 up to one million. Calculated parameters of $x_0$ were plotted versus the number of templates showing the PCR standard curve (see FIG. 11, FIG. 12).

Figure 13:
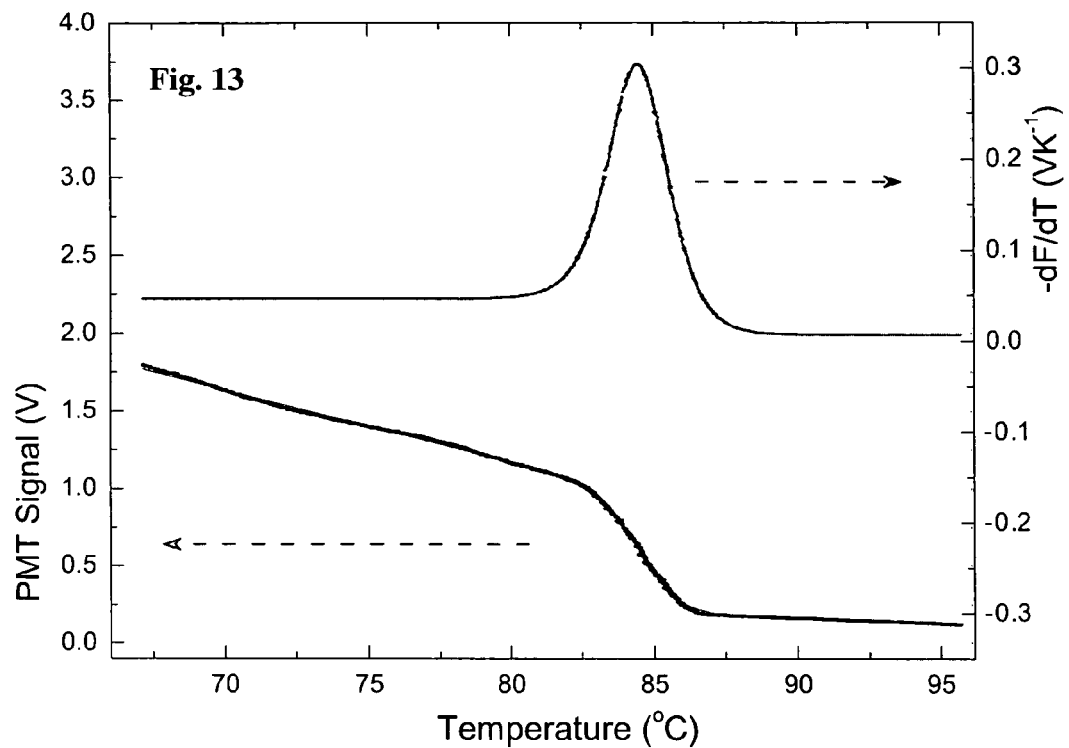
FIG. 13 depicts the fluorescence signal from a melting curve analysis and its approximation by the sigmoid function $$y = \frac{(A_0 - x)(A_1 - A_2)}{1 + \exp\left(\frac{x - x_0}{k}\right)} + A_2 + A_3 x$$

As indicated above, after thermal cycling of the PCR device a melting curve analysis (Fixman, M, Freire, J. J., Biopolymers, 1977, 16, 2693-2704; Wilkening, S., Bader, A., J. of Biomolecular techniques, 2004, 15, 107-111; Lyon, E., et al., Clinical Chemistry, 2001, 47, 844-850) was performed in order to determine the purity of the PCR (cf. FIG. 13). The fluorescence signal was approximated by a modified sigmoidal function:

$$y = \frac{(A_0 - x)(A_1 - A_2)}{1 + \exp\left(\frac{x - x_0}{k}\right)} + A_2 + A_3 x, \quad (4)$$

where $A_0$, $A_1$, $A_2$ and $A_3$ as well as $x_0$ and k have identical functions as in Eq. (3).

The fitting error shows only a small difference between the measured data and the fitting curve, showing that there is only one PCR product with a limited amount of byproducts. The purity of products was proven by the results of capillary electrophoresis (see FIG. 14).

What is claimed is:

1. An apparatus comprising:
   a) at least one temperature module comprising
      i. a heater,
      ii. a conductor of caloric comprised of a material selected from the group consisting of a metal, a semiconductor, a diamond, a carbon nanotube, and a fullerene, and
      iii. a temperature sensor,
   wherein the heater and the temperature sensor each comprise a surface arranged on a common plane and are arranged concentrically with respect to each other in a top view, and
   b) a removable substrate having a top surface structure to receive a sample selected from the group consisting of a chemical sample, a biological sample and a combination thereof in liquid form, the substrate being arranged on a plane parallel to the common plane, and a bottom surface structured to be in contact with the conductor of caloric;
   wherein the apparatus defines a substrate-supporting surface configured to position the substrate above and entirely covering the temperature control module and to secure the substrate solely by the force of gravity;
   wherein the heater is in thermal communication with the substrate via the conductor of caloric; and
   wherein the temperature sensor is adapted to detect and control the temperature of the substrate via the conductor of caloric.

2. The apparatus of claim 1, wherein said heater comprises a surface that is arranged essentially parallel to the plane of said substrate, on which plane a substrate top surface is arranged to receive said sample.

3. The apparatus of claim 1, wherein said sensor comprises a surface that is arranged essentially parallel to the plane of said substrate, on which plane a substrate top surface is structured to receive said sample.

4. The apparatus of claim 1, wherein the heater surrounds the sensor.

5. The apparatus of claim 1, comprising at least two temperature control modules, wherein the at least two temperature control modules are thermally isolated from each other.

6. The apparatus of claim 5, wherein the at least two temperature control modules comprise each a surface arranged in a common plane, which is essentially parallel to the plane of said substrate, on which plane a substrate top surface is arranged to receive said sample.

7. The apparatus of claim 6, wherein said two temperature control modules are opposing each other in said plane that is essentially parallel to the plane of said substrate, on which plane a substrate top surface is arranged to receive said sample.

8. The apparatus of claim 7, comprising two pairs of temperature control modules, wherein the two temperature control modules of each pair are opposing each other in said plane that is essentially parallel to the plane of said substrate, on which plane a substrate top surface is arranged to receive said sample.

9. The apparatus of claim 5, wherein the at least two temperature control modules comprises a plurality of temperature control modules, wherein each temperature control module is thermally isolated from every other temperature control module.

10. The apparatus of claim 1, wherein the sensor is made of a metal or a metal alloy.

11. A method for regulating the temperature of a sample selected from the group consisting of a chemical sample, a biological sample and a combination thereof, comprising the steps of:
  a) providing an apparatus comprising:
    i) at least one temperature module comprising
      A) a heater,
      B) a conductor of caloric comprised of a material selected from the group consisting of a metal, a semiconductor, a diamond, a carbon nanotube, and a fullerene, and
      C) a temperature sensor,
    wherein the heater and the temperature sensor each comprise a surface arranged on a common plane and are arranged concentrically with respect to each other in a top view, and
    ii) a removable substrate having a top surface structured to receive a sample selected from the group consisting of a chemical sample, a biological sample and a combination thereof in liquid form, the substrate being arranged on a plane parallel to the common plane, and a bottom surface structured to be in contact with the conductor of caloric;
    wherein the apparatus defines a substrate supporting-surface configured to position the substrate above and entirely covering the temperature control module and to secure the substrate solely by the force of gravity;
    wherein the heater is in thermal communication with the substrate via the conductor of caloric; and wherein the temperature sensor is adapted to detect and control the temperature of the substrate via the conductor of caloric, and
  b) providing to the apparatus a temperature value for heating the sample,
  c) measuring the temperature of said conductor of caloric of the apparatus by means of the temperature sensor of the apparatus, and
  d) applying heat to the conductor of caloric when the measured temperature is below the temperature value, thereby regulating the temperature of the sample.

12. The method of claim 11, wherein the sample is comprised in a liquid droplet.

13. The method of claim 11, wherein said apparatus for regulating the temperature of a sample selected from the group consisting of a chemical sample, a biological sample, and a combination thereof comprises at least two temperature control modules, wherein the at least two temperature control modules are thermally isolated from each other.

14. The method of claim 13, wherein an individual temperature value is provided for heating the sample at each temperature control module, and wherein the temperature of the conductor of caloric of each temperature control module is measured individually by means of said temperature sensor of each temperature control module, and
  wherein heat is applied to the conductor of caloric of each temperature control module as long as the measured temperature is below the provided temperature value, thereby heating each substrate and the sample individually.

15. The method of claim 11, wherein providing an apparatus for regulating the temperature of a sample selected from the group consisting of a chemical sample, a biological sample, and a combination thereof, the apparatus comprising a temperature module, comprises the steps:
  a) providing a substrate,
  b) disposing said substrate above said temperature control module, such that it entirely covers the same,
  c) providing a sample selected from the group consisting of a chemical sample, a biological sample, and a combination thereof, and
  d) disposing the sample onto a top surface of said substrate.

16. The method of claim 11, wherein the sample is selected from the group consisting of a soil sample, an air sample, an environmental sample, a cell culture sample, a bone marrow sample, a rainfall sample, a fallout sample, a space sample, an extraterrestrial sample, a sewage sample, a ground water sample, an abrasion sample, an archaeological sample, a food sample, a blood sample, a serum sample, a plasma sample, a urine sample, a stool sample, a semen sample, a lymphatic fluid sample, a cerebrospinal fluid sample, a naspharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a nail sample, a hair sample, a skin sample, a cancer sample, a tumour sample, a tissue sample, a cell sample, a cell lysate sample, a virus culture sample, a forensic sample, an infection sample, a nosocomial infection sample, a production sample, a drug preparation sample, a biological molecule production sample, a protein preparation sample, a lipid preparation sample, a carbohydrate preparation sample, a solution of a nucleotide, a solution of polynucleotide, a solution of a nucleic acid, a solution of a peptide, a solution of a polypeptide, a solution of an amino acid, a solution of a protein, a solution of a synthetic polymer, a solution of a biochemical composition, a solution of an organic chemical composition, a solution of an inorganic chemical composition, a solution of a lipid, a solution of a carbohydrate, a solution of a combinatory chemistry product, a solution of a drug candidate molecule, a solution of a drug molecule, a solution of a drug metabolite, a suspension of a cell, a suspension of a virus, a suspension of a microorganism, a suspension of a metal, a suspension of metal alloy, a solution of a metal ion, and any combination thereof.

17. The method of claim 11, wherein heating the sample includes carrying out a process selected from the group consisting of a chemical process, a biological process, and a combination thereof.

18. The method of claim 17, wherein the sample includes a nucleic acid molecule and the process is a polymerase chain reaction.

* * * * *